US006855791B2

(12) United States Patent
Van Doren et al.

(10) Patent No.: US 6,855,791 B2
(45) Date of Patent: Feb. 15, 2005

(54) PROCESS AND APPARATUS FOR IMPROVING AND CONTROLLING THE VULCANIZATION OF NATURAL AND SYNTHETIC RUBBER COMPOUNDS

(75) Inventors: John C. Van Doren, Bailey, CO (US); Richard Magill, Broomfield, CO (US); Bruce Sellers, Golden, CO (US); Tim Erickson, Littleton, CO (US); Scott Schnieder, Aurora, CO (US); Steve Courington, Lone Tree, CO (US); Lance Bethel, Westminster, CO (US)

(73) Assignee: Signature Control Systems, Denver, CO (US)

( * ) Notice: Subject to any disclaimer, the term of this patent is extended or adjusted under 35 U.S.C. 154(b) by 0 days.

(21) Appl. No.: 10/267,197

(22) Filed: Oct. 8, 2002

(65) Prior Publication Data

US 2004/0010068 A1 Jan. 15, 2004

Related U.S. Application Data

(60) Provisional application No. 60/394,736, filed on Jul. 9, 2002.

(51) Int. Cl.[7] ................................................. C08F 36/00
(52) U.S. Cl. .................... 526/335; 156/338; 264/171.1; 264/216; 264/331.13; 374/1; 73/861.14
(58) Field of Search .................... 526/335; 156/338; 264/171.1, 216, 331.13; 374/1; 73/861.14

(56) References Cited

U.S. PATENT DOCUMENTS

| | | | |
|---|---|---|---|
| 2,765,219 A | 10/1956 | Shawhan | 23/253 |
| 3,746,975 A | 7/1973 | Malthy | 324/65 R |
| 3,753,092 A | 8/1973 | Ludlow et al. | 324/61 R |

(List continued on next page.)

FOREIGN PATENT DOCUMENTS

| | | | |
|---|---|---|---|
| EP | 0 540 103 B1 | 2/1996 | C08K/5/3415 |
| EP | 0 743 153 A1 | 11/1996 | B29C/35/02 |
| EP | 1 050 888 A1 | 11/2000 | H01B/1/20 |
| WO | WO 99/13346 | 3/1999 | G01R/27/04 |

OTHER PUBLICATIONS

U.S. patent application Ser. No. 10/102,614, Magill, filed Mar. 19, 2002.
U.S. patent application Ser. No. 09/815,342, Van Doren et al., filed Mar. 21,2001.
"Automatic, Computer Controlled, Processing of Advanced Composites"; *Defense Small Business Innovation Research (SBIR) Program*; Apr. 7, 1988; 25 pgs.
Baumgartner et al.; "Computer Assisted Dielectric Cure Monitoring in Material Quality and Cure Process Control"; *SAMPE Journal*; Jul./Aug. 1983; pp. 6–16.
Buczek; "Considerations in the Dielectric Analysis of Composites"; *40th International SAMPE Symposium*; May 8–11, 1995; pp. 696–710.
Buczek; "Self–Directed Process Control System for Epoxy Matrix Composites"; *40th International SAMPE Symposium*; May 8–11, 1995; 8 pgs.

(List continued on next page.)

*Primary Examiner*—William K. Cheung
(74) *Attorney, Agent, or Firm*—Sheridan Ross P.C.; Dennis J. Dupray

(57) ABSTRACT

A process for curing a natural or synthetic rubber includes the measuring of curing conditions by dielectric or impedance means to produce a process curve (impedance property data versus time) followed by analyzing the process curve with a software algorithm which defines and statistically quantifies the correlation between the process curve and the desired part properties. The correlation relationship is applied in real time to end the curing process at the optimum time and to produce rubber parts of uniform quality and with reduced process cycle time.

30 Claims, 11 Drawing Sheets

U.S. PATENT DOCUMENTS

| | | | |
|---|---|---|---|
| 3,778,705 A | 12/1973 | Malthy | 324/61 R |
| 3,781,672 A | 12/1973 | Malthy et al. | 324/61 R |
| 3,879,644 A | 4/1975 | Malthy | 317/246 |
| 3,985,712 A | 10/1976 | Garst | 260/75 M |
| 4,331,516 A | 5/1982 | Meighan | 204/2.1 |
| 4,338,163 A | 7/1982 | Rittenhouse | 204/2.1 |
| 4,344,142 A | 8/1982 | Diehr, II et al. | 364/473 |
| 4,373,092 A | 2/1983 | Zsolnay | 528/481 |
| 4,381,250 A | 4/1983 | Rittenhouse | 252/182.1 |
| 4,399,100 A | 8/1983 | Zsolnay et al. | 422/62 |
| 4,423,371 A | 12/1983 | Senturia et al. | 324/61 R |
| 4,433,286 A | 2/1984 | Capots | 324/61 R |
| 4,448,943 A | 5/1984 | Golba et al. | 526/59 |
| 4,496,697 A | 1/1985 | Zsolnay et al. | 526/60 |
| 4,510,103 A * | 4/1985 | Yamaguchi et al. | 264/408 |
| 4,510,436 A | 4/1985 | Raymond | 324/61 P |
| 4,515,545 A | 5/1985 | Hinrichs et al. | 425/143 |
| 4,551,103 A | 11/1985 | Vitale | 434/225 |
| 4,551,807 A | 11/1985 | Hsich et al. | 364/473 |
| 4,676,101 A | 6/1987 | Baughman | 73/304 C |
| 4,723,908 A | 2/1988 | Kranbuehl | 432/37 |
| 4,773,021 A | 9/1988 | Harris et al. | 364/476 |
| 4,777,431 A | 10/1988 | Day et al. | 324/61 P |
| 4,868,769 A | 9/1989 | Persson | 364/550 |
| 4,881,025 A | 11/1989 | Gregory | 324/61 R |
| 5,008,307 A | 4/1991 | Inomata | 523/220 |
| 5,032,525 A | 7/1991 | Lee et al. | 436/55 |
| 5,184,077 A | 2/1993 | Day et al. | 324/693 |
| 5,201,956 A | 4/1993 | Humphrey et al. | 118/716 |
| 5,207,956 A | 5/1993 | Kline et al. | 264/40.6 |
| 5,208,544 A | 5/1993 | McBrearty et al. | 324/687 |
| 5,219,498 A | 6/1993 | Keller et al. | 264/40.2 |
| 5,223,796 A | 6/1993 | Waldman et al. | 324/687 |
| 5,283,731 A | 2/1994 | Lalonde et al. | 364/401 |
| 5,317,252 A | 5/1994 | Kranbuehl | 324/71.7 |
| 5,453,689 A | 9/1995 | Goldfine et al. | 324/239 |
| 5,459,406 A | 10/1995 | Louge | 324/688 |
| 5,486,319 A | 1/1996 | Stone et al. | 264/406 |
| 5,521,515 A | 5/1996 | Campbell | 324/674 |
| 5,528,155 A | 6/1996 | King et al. | 324/713 |
| 5,569,591 A | 10/1996 | Kell et al. | 435/29 |
| 5,749,986 A | 5/1998 | Wyatt | 156/64 |
| 5,872,447 A | 2/1999 | Hager, III | 324/71.1 |
| 5,874,832 A | 2/1999 | Gabelich | 324/689 |
| 5,898,309 A | 4/1999 | Becker et al. | 324/689 |
| 5,961,913 A | 10/1999 | Haase | 264/326 |
| 5,996,006 A | 11/1999 | Speicher | 709/218 |
| 6,043,308 A | 3/2000 | Tanahashi et al. | 524/495 |
| 6,472,885 B1 | 10/2002 | Green et al. | 324/638 |

OTHER PUBLICATIONS

"Critical Point Control/Statistical Quality Control Software Module"; *Micromet Instruments*; 1993; 2 pgs.

Desanges; "Changes in the Electrical Properties of Natural Rubber/Carbon Black Compounds During Vulcanization"; *Revue Generale du Caoutchouc*; Dec. 1957; 34(12); pp. 631–649.

"Dielectric Cure Testing on Polyester Bulk Molding Compound"; *Holometrix Micromet*; 2001; 3 pgs. http://www.holometrix.com/holometrix/m_materialtest.asp.

"Dielectric Sensors"; *NETZSCH*; Feb. 21, 2002; pgs.

"Eumetric System III Microdielectrometer . . ."; *Holometrix Micromet*; 2001; 5 pgs.

"ICAM–1000—In–mold Monitoring For SPC, SQC, and CPC (Critical Point Control) of Thermoset Molding Operations"; *Micromet Instruments, Inc.*; at least as early as Mar. 1990; 4 pgs.

"ICAM–1000 Industrial Cure Analysis & Monitoring System"; *Micromet Instruments, Inc.*; Aug. 1, 1991, 1 pg.

"ICAM–2000 Multi–Channel Cure Analyzer"; *Micromet Instruments*; 1993; 2 pgs.

Johnson et al.; "Production Implementation of Fully Automated, Closed Loop cure Control for Advanced Composite Strucutres"; *34$^{th}$International SAMPE Symposium*; May 8–11, 1989; pp. 373–384.

Keller et al.; "Computer Controlled Processing of Composites Utilizing Dielectric Signature Curves"; *SAMPE Journal*; Sep./Oct. 1992; 28(5); pp. 25–33.

Keller et al.; "Real Time, In–Situ Dielectric Monitoring of Advanced Composites Curing Processes"; *Programmed Composites, Inc.*; Aug. 1, 1987, 63 pgs.

Khastqir, "A Comparative Study of Step Curing and Continuous Curing Methods"; *Rubber World*; Jan. 1994; pp. 28–31.

"Lockheed Signature Process Control for Composites Proposal"; *Ketema Programmed Composites, Inc.*; Jul. 1, 1993; pp. 1–12.

"MDE Series 10 Cure Monitor"; *Holometrix Micromet*; at least as early as Mar. 15, 2000; 2 pgs.

"Mono–Probe"; *TYT–NAM–MON*; Oct. 27, 2000; 1 pg.

"Northrop Aircraft Division RTM System Proposal"; *Ketema Programmed Composites, Inc.*; Apr. 1, 1993, 13 pgs.

O'Conor et al.; "Update to the June 1990 Confidential Descriptiive Memorandum"; *Micromet Instrument, Inc.*; Dec. 1, 1990; 17 pgs.

Persson; "A Novel Method of Measuring Cure—Dielectric Vulcametry"; *Plastics and Rubber Processing and Applications*; 1987; 7(2); pp. 111–125.

"Product Selection Grid"; *Holometrix Micromet*; 2001: 1 pg.; http://www.holometrix.com/holometrix/m_prgrid.asp.

Rajeshwar; "AC Impedance Spectroscopy of Carbon Black–Rubber Composites"; *Department of Chemistry and Biochemistry at The University of Texas as Arlington*; Sep. 21–24, 1999; 13 pgs.

SmartTrac Advertisement, *Automotive News*; May 21, 2001, 1 pg.

"SmartTrac"; *Innovative Aftermarket Systems, Inc.*; 2001; 2 pgs. http://www.ias–inc.net/pages/products/smart.html.

"Textron Aerostructures Autoclave Process Control Proposal"; *Keterna Programmed Composites, Inc.*; Feb. 12, 1993; 16 pgs.

"The Eumetric System III Microdielectrometer"; *Micromet Instruments, Inc.*; Sep. 1991; 4 pgs.

"Thermokinetics"; *NETZSCH*; Nov. 8, 2001; 2 pgs.

"Tool Mount Sensors"; *NETZSCH*; Feb. 21, 2002; 2 pgs.

"Vulcanization of Natural Rubber"; *NETZSCH*; Nov. 8, 2001; 2 pgs.

"Notification of Transmittal of the International Search Report or the Declaration" from the Patent Cooperation Treaty in International patent application No. PCT/US02/32480 filed Oct. 9, 2002.

* cited by examiner

LEGEND:

o  Data Point (intersection of algorithm determined time with rheometrically determined cure time.

── Best Fit through the Data Points

······ 95% Confidence Intervals

LEGEND:

o   Data Point (intersection of algorithm determined time with rheometrically determined cure time.

───   Best Fit through the Data Points

......   95% Confidence Intervals

PROCESS AND APPARATUS FOR IMPROVING AND CONTROLLING THE VULCANIZATION OF NATURAL AND SYNTHETIC RUBBER COMPOUNDS

RELATED FIELD OF THE INVENTION

This invention relates to a new and improved process and apparatus for monitoring and controlling the vulcanization of natural and synthetic rubber compounds containing fillers such as carbon black, oils, clay, and the like. Typical base rubber polymers which may be employed include styrene-butadiene, polybutadiene, polyisoprene, ethylene-propylene, butyl, halobutyl, nitrile, polyacrylic, neoprene, hypalon, silicone, fluorcarbon elastomers, polyurethane elastomers, and mixtures thereof.

BACKGROUND OF THE INVENTION

Heretofore methods of applying fixed process parameters to the processing of polymeric rubber compounds during vulcanization have resulted in both reduced productivity due to overly conservative cure times and poor product uniformity due to the inability of the fixed process parameters to accommodate the inherent variability in the process.

The relationship of dielectric properties and the state and rate of the cure of polymers well known. Related publications in this field include:

U.S. PATENT DOCUMENTS

| | | |
|---|---|---|
| 4,344,142 | August 1982 | Diehr,II et al. |
| 4,373,092 | February 1983 | Zsolnay |
| 4,399,100 | August 1983 | Zsolnay, et al. |
| 4,423,371 | December 1983 | Senturia, et al. |
| 4,496,697 | January 1985 | Zsolnay, et al. |
| 4,510,103 | April 1985 | Yamaguchi, et al. |
| 4,551,807 | November 1985 | Hinrichs, et al. |
| 4,723,908 | February 1988 | Kranbuehl |
| 4,777,431 | October 1988 | Day, et al. |
| 4,773,021 | September 1988 | Harris, et al. |
| 4,868,769 | September 1989 | Persson, et al. |
| 5,032,525 | July 1991 | Lee, et al. |
| 5,219,498 | June 1993 | Keller, et al. |
| 5,317,252 | May 1994 | Kranbuehl |
| 5,486,319 | January 1996 | Stone, et al. |
| 5,528,155 | June 1996 | King, et al. |
| 5,872,447 | February 1999 | Hager, III |

Other Publications

*Changes in the Electrical Properties of Natural Rubber/Carbon Black Compounds during Vulcanization*, 1957, H. Desanges, French Rubber Institute

*A novel method of measuring cure—dielectric vulcametry*, 1986, Sture Persson, The Plastics and Rubber Institute, England

*A comparative study of step curing and continuous curing methods*, 1994, D. Khastgir, Indian Institute of Technology

*AC Impedance Spectroscopy of Carbon Black-Rubber composites*, 1999, K. Rajeshwar, University of Texas at Arlington The prior art has clearly established the relationship between the dielectric (herein also referred to as "impedance") properties of polymeric resins which exhibit rheometric and chemical behavior such as melt, volatile release, gelation, and crosslinking that can be recognized by dielectric means for those skilled both in the art and those resins' physical properties. However, unlike polymeric resins, polymeric rubber compounds do not melt or exhibit gelation during cure or vulcanization and are therefore much more difficult to characterize, monitor and control by dielectric means. Moreover, none of the prior art associated with polymeric rubber curing (also referred to as "vulcanization") addresses the practical aspects of taking measurements directly in the production process, especially in the highly abrasive and high pressure environment of injection molding. Additionally the prior art does not show how to use the electrical data obtained to achieve closed-loop control of the curing or vulcanization process over a wide range of molding methods and conditions.

The prior art also does not show how to compensate the vulcanization process for variations in compound from batch to batch and within batches, and for differences in vulcanizate thickness. Additionally, the prior art does not compensate for additional variables, which are introduced into the process by the nature of the vulcanization equipment, tooling, and thermal history of the compound.

Moreover, the prior art uses dielectric or impedance measuring apparatus, which employ opposing and parallel electrodes of precise area and separation distance, and in which, the electrodes are in direct contact with the rubber compound. Although such electrodes and apparatus provide a means for measuring impedance properties during cure, they are entirely impractical for use in a production environment. For example, many rubber components are produced using injection molding technology which subjects the sensors to pressures up to 30,000 psi and temperatures up to 425° F. Moreover, due to the flow inside the mold during injection, in addition to the carbon and silica fillers present in many rubber compounds, the sensor must survive in a highly abrasive environment. Finally, the sensor must also be able to survive mold cleaning via typical cleaning methods such as $CO_2$ and plastic bead blast.

Accordingly, it is desirable to have an apparatus and method for alleviating the above described drawbacks to using impedance data measurements for monitoring and controlling the vulcanization process. In this case, the impedance sensor provided at the vulcanization equipment is both extremely rugged and more easily used in that the electrodes need not be of precise area, need not be of precise separation distance from one another, need not be in direct contact with the material being vulcanized. In addition, a method is established for correlating the desired properties of the rubber product with the impedance measurements.

Definitions and Terms

Numerous technical terms and abbreviations are used in the description below. Accordingly, many of these terms and abbreviations are described in this section for convenience. Thus, if a term is unfamiliar to the reader, it is suggested that this section be consulted to obtain a description of the unknown term.

Rubber Polymeric Compounds: Typical base rubber polymeric compounds which may be employed include styrene-butadiene, polybutadiene, polyisoprene, ethylene-propylene, butyl, halobutyl, nitrile, polyacrylic, neoprene, hypalon, silicone, fluorcarbon elastomers, polyurethane elastomers, and mixtures thereof.

ODR: Oscillating Disk Rheometer—Device that measures the rheological characteristics (elastic torque, viscous torque, etc.) of a polymer during vulcanization, using an oscillating disk to apply stress to the curing polymer.

MDR: Moving Die Rheometer—Device that measures the rheological characteristics (elastic torque, viscous torque, etc.) of a polymer during vulcanization, using a moving die to apply stress to the curing polymer.

Rheometric instrument: Device that measures the rheological characteristics (elastic torque, viscous torque, etc.) of a polymer during vulcanization.

T90 Time: The time, as measured in an ODR or MDR at which a given rubber compound at a given curing temperature, reaches 90% of its ultimate elastic torque value.

Designed Experiment: A single set of actual related experiments drawn up from one of the types of designs to be found in the body of methods for design of experiments.

Exponential Dampening: The damping coefficient ($\alpha$) as defined by a best exponential fit to a set of raw data, where the fit curve (y) is described by the equation $y=Ae^{\alpha t}$, where t is time.

Exponential Amplitude Coefficient: The amplitude coefficient (A) as defined by a best exponential fit to a set of raw data, where the fit curve (y) is described by the equation $$y=Ae^{-\alpha t}, \text{ where t is time.}$$

Topological Features of Impedance Related Data: Recognizable and distinct features within a cure curve, such as a peak (maxima), valley (minima) or flat (no slope).

Low CTE Metallic Material: Material with low coefficient of thermal expansion.

Tool Steel: A steel suitable for use in making injection and compression molds such as AISI Type A2 Tool Steel.

Witness cavity: A small cavity for in-mold vulcanization measurement, whereby the dielectric sensor does not directly sense any of the parts that are being produced. Instead, the sensor monitors the cure in the "witness" location.

R-square ($R^2$): R-square (also known as the coefficient of determination) is a statistical measure of the reduction in the total variation of the dependent variable due to the independent variables. An R-square close to 1.0 indicates that the model (as used herein, the algorithm) accounts for almost all of the variability in the respective variables.

Confidence interval: A range of values within which a particular number of interest is calculated to fall, at some specific level of probability such as 95%.

SUMMARY OF THE INVENTION

The present invention is a method and system for controlling the vulcanization (herein also denoted "curing") of rubber polymeric compounds. In particular, the present invention includes novel features for monitoring the polymerization and determining in real-time the optimum cure time for the production of parts made from rubber polymeric compounds (herein also denoted as merely "rubber compounds"). According to the present invention, during the curing of rubber polymeric compounds distinctive impedance property versus time graphs (herein also denoted "process curves") may be obtained from one or more capacitor circuits operatively configured so that such a rubber polymeric compound for curing becomes part of each such capacitor circuit, and in particular, becomes a dielectric for such circuits. More specifically, the present invention utilizes, e.g., shape or curve characteristics of the impedance (Z), phase angle (ø), resistance (R), reactance (X), conductance (G), or capacitance (C) versus time graphs derived from the signal responses output by the activation of one or more of these capacitor circuits, wherein such activation is the result of at least one, and more generally, a plurality of different signals being input to such capacitor circuits. Thus, in some embodiments of the present invention, the shape (or other computational characteristics) of a corresponding process curve for each of a plurality of different signal frequencies input to the capacitor circuits may be used in monitoring, controlling and/or predicting an outcome of a curing process.

In some embodiments of the present invention, various time series capacitor circuit output data components (i.e., impedance (Z), phase angle (ø), resistance (R), reactance (X), conductance (G), or capacitance (C)) are separately processed, thereby resulting in a process curve with distinctive shape (or other features) for each of these components. Accordingly, it is an aspect of the present invention that such features from impedance (Z), phase angle (ø), resistance (R), reactance (X), conductance (G), or capacitance (C) graphs (e.g., plotted versus time) can be used for monitoring and controlling the cure time by measuring a portion of the process curve and calculating or predicting the optimum cure time. Thus, since a particular shape (or other computational feature) of such process curves may be substantially repeatable for curing a particular material, such features can be effectively utilized in a mass production environment for producing consistent high quality cured products (e.g., seals, gaskets, and tires).

Moreover, it is a further aspect of the present invention that for a given material to be cured, the invention can identify at least some of the computational features of these process curves substantially independently of the configuration of the product being produced via the use of a "witness cavity" incorporated into the runner system of the mold, as one skilled in the art will understand. In particular, such computational features can be correlated with the chemical and rheometric changes occurring during the curing process.

Thus, although such process curves may vary in amplitude and duration (e.g., due to cured part thickness, thermal history, mold temperature and heat rate, curative level, compound batch variations, and various other factors), the present invention may be used for monitoring, controlling and/or predicting cure states of products in a mass production environment wherein the products being produced may be subject to significant process and rubber compound variation.

For example, for a particular sample or product to be cured, properties of one or more of the above described process curves can be calculated for a specific measurement period wherein the portion of the data corresponding to the process curve of the sample may be correlated to a desired final cure state of the product, and accordingly, such a correlation can be used to establish a time for appropriately curing a part in production. In particular, the present invention predicts cure times as will be described more fully herein below. It is a further aspect of the present invention, that for certain rubber compounds, the corresponding shape of one or more of the above described process curves may exhibit a "maxima" and/or a "minima" at a given time which can also be used to infer useful information in monitoring, controlling and/or predicting the cure time.

It is a further aspect of the present invention that embodiments thereof include signal processing and other software and hardware ("components") for both deriving such computational features of the process curves obtained from a rubber compound being cured, and utilizing such features to determine in real-time the optimum cure time for each production cure cycle.

Moreover, it is an aspect of the present invention that such cure times are determined to achieve a desired property such as tensile strength, dynamic stiffness, or compression set in the resulting cured part.

Additional aspects, features and benefits of the present invention will become evident from the accompanying drawings and the detailed description herein below.

DESCRIPTION OF THE PREFERRED EMBODIMENTS

Key Elements:

The scope of the invention can fundamentally be broken into five key elements, which together form the equipment and tools necessary for use of the impedance property monitoring in injection and other rubber molding environments such as compression molding, transfer molding, and the like. These elements are described as follows:

(1) Production-capable sensor
(2) Sensor circuit (non-bridged)
(3) Demodulation methodology for the sensor signal
(4) Methodology for establishing control algorithms
(5) Real-time control application Element 1: Production-Capable Sensor The prior art uses dielectric or impedance measuring apparatus that employ opposing and parallel electrodes of precise area and separation distance. Additionally, the metallic electrodes are typically in direct contact with the rubber compound. Although such electrodes and apparatus provide a means for measuring impedance properties during cure, they are entirely impractical for use in a production environment. For example, many rubber components are produced using injection-molding technology that subjects the sensors to pressures up to 30,000 psi and temperatures up to 425° F. Moreover, due to the flow inside the molds during injection, and the carbon and silica fillers present in many rubber compounds, the sensor must survive in a highly abrasive environment. Finally, the sensor must be able to survive mold cleaning via the use of $CO_2$ bead blast, plastic bead blast, and the like.

Accordingly, it is desirable to have a sensor for alleviating the above described drawbacks to using in-situ impedance data for monitoring and controlling the vulcanization process, wherein the impedance sensor provided at the vulcanization equipment is both extremely rugged and more easily used in that the electrodes need not be of precise area, need not be of precise separation distance from one another, and need not be in direct contact with the material being vulcanized. Thus, as will be described hereinbelow, the impedance measuring components of the present invention not only includes a production capable sensor, but also may include at least portions of the vulcanization equipment and its associated tooling, wherein such vulcanization equipment can include: injection molding machines, compression and transfer molding presses, belt making presses, autoclaves, tire molding machines, and the like. Additionally, such associated tooling can include: injection molds, compression and transfer molds, mandrels, platens, tire molds, and the like, as one skilled in the art will understand.

Figure 2:
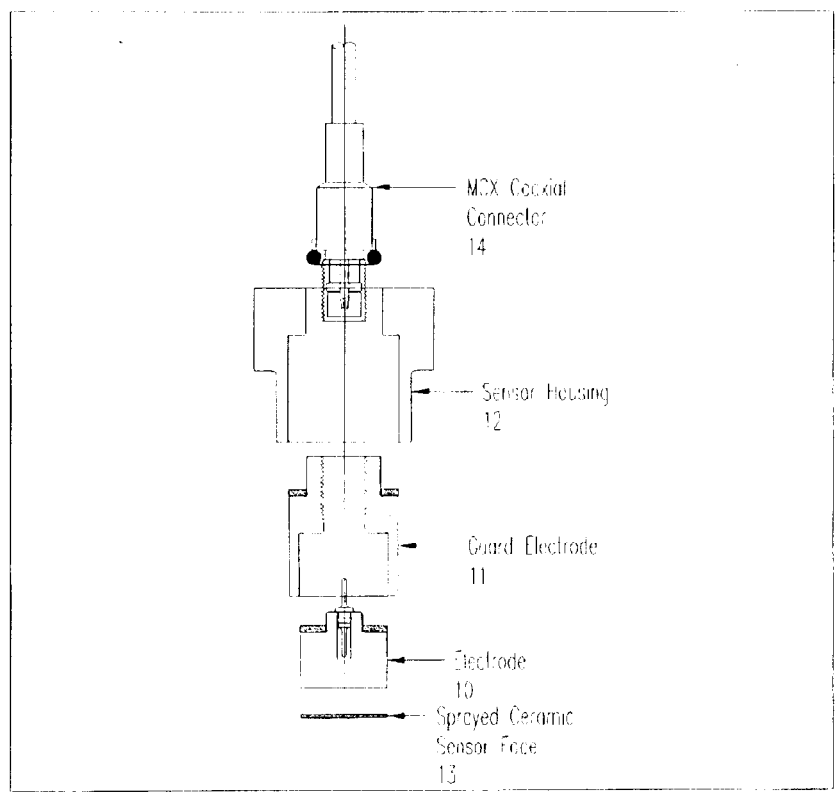
FIG. 2 Shows an exploded view of one embodiment of the sensor.

The impedance sensor that meets these requirements includes a primary electrode 10 that serves as a capacitor plate. An additional capacitor, acting as a guard electrode 11, rings the primary electrode of each sensor. The guard electrode 11, which is excited along with the electrode 10 helps to preclude the field induced at the primary electrode 10 of the sensor from fringing or becoming non-linear. Both electrodes may be a low CTE metallic material, such as Kovar, embedded in a layered ceramic circuit using methods developed by Lamina Ceramics of Princeton, N.J. or in another embodiment shown in FIG. 2, a nested construction of A2 tool steel components consisting of a housing 12, primary electrode 10, and guard electrode 11 that are separated radially by a cyanate ester potting material and axially by a thin ceramic coating such as alumina ceramic or like material. The alumina ceramic coating is applied with a thermal spray process (i.e. detonation gun, plasma, or HVOF spray, as is well known by those skilled in the art) that provides electrical isolation and transmits the compressive loads generated by the process. In addition, the electrode and guard are separated from the rubber compound being cured by a dielectrically stable material such as a thin coating of alumina ceramic 13 or like material applied with a detonation gun or other high velocity ceramic spray process, wherein the material is dielectrically stable over the temperature range of the vulcanizing process (e.g., 300° F. to 425° F.). A coaxial cable is connected to the sensor via an MCX connector such as Johnson Components' MCX connector 14, p.n. 133-833-401 which is screwed into the guard. The center conductor mates with a pin machined integral wth or press fit into the electrode. In another embodiment of the sensor described in FIG. 2, the primary electrode 10, guard electrode 11, and housing 12, along with an alumina ceramic face may be fused together and separated electrically with glass or glass doped with alumina ceramic. In another embodiment of the sensor described in FIG. 2, the primary electrode 10, guard electrode 11, and housing 12 may be coated with a diamond or diamond-like 2–4 micron coating such as Casidium as supplied by Anatech Ltd of Springfield, Va. and then press fit together such that the diamond or diamond-like coating provides electrical isolation between the three elements and between the rubber compound and the face of the sensor.

Therefore the production-ready sensor is an extremely rugged device, capable of survival in a high pressure, high abrasion, and high temperature environment. The fundamental electrical function of the sensor is to act as a guarded or shielded electrode, forming a single plate of a capacitor. Any other planar or semi-planar conductive surface within the interior of the vulcanizing equipment can serve as the opposing electrode plate of the capacitor. Note that the opposing plate acts as the third electrode of the capacitor, and thus the opposing plate electrically couples with the primary electrode. Further note that the opposing plate is grounded 25 to provide a common signal reference point.

Figure 1:
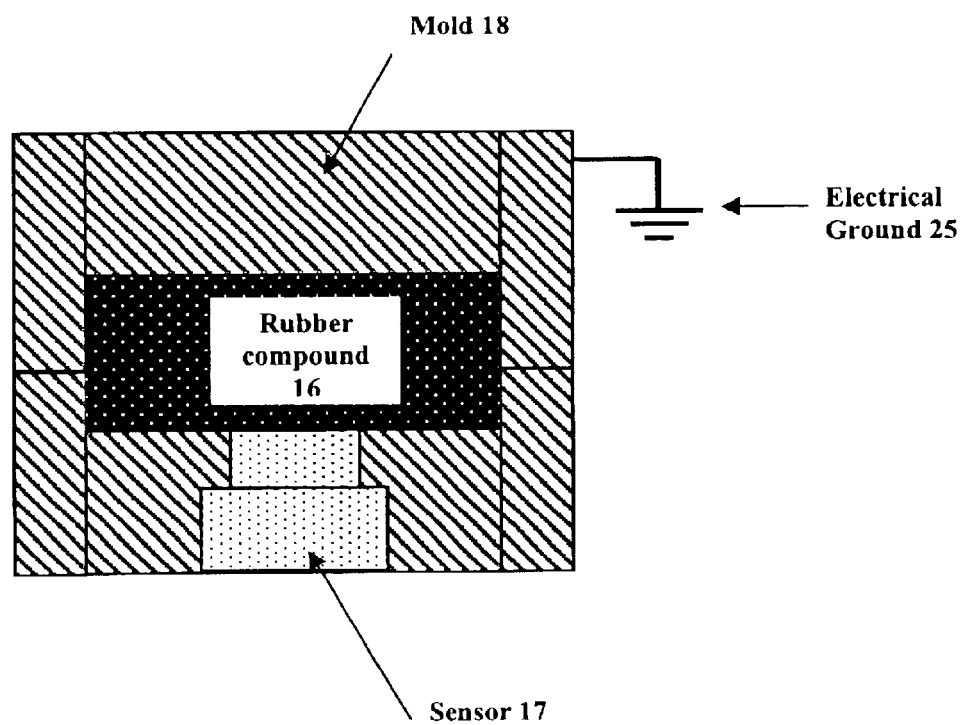
FIG. 1 Shows the sensor arrangement schematically in a mold.

The vulcanizing rubber compound 16 in the injection mold 18 then becomes the dielectric within the formed capacitor, as it is sandwiched between the sensor 17 and the surface of the mold 18 or metallic insert within the part being molded (the opposing electrode). Since the dielectric properties of the rubber change as the rubber vulcanizes, the impedance of the formed capacitor changes as well, which allows for a non-invasive method of monitoring and controlling vulcanization in the mold 18. FIG. 1 shows the sensor arrangement schematically in a mold 18.

The sensor may be flush mounted in the mold in contact with the part being molded or located in contact with the runner system feeding the part cavity, or alternately may be located in contact with a "witness cavity". A witness cavity is a small cavity that is machined into the mold to allow the sensor to measure rubber cure without the sensor being in direct contact with the curing part. In some applications, the parts are too small or the dimensional specifications are too strict to allow sensor placement directly on the part. In these cases, a witness cavity is machined into available space in the mold and the sensor monitors curing in the witness cavity. For example, the witness cavity may be placed in the injection runner system of a mold. Since this rubber is from the same batch, sees the same mold temperature, and experiences the same heat history, it provides a good representation of curing behavior observed in the part itself. In addition, more than one sensor can be used to monitor the process, and the lagging sensor from cycle to cycle can be used to control the end point of any given cure cycle.

Element 2: Sensor Circuit (Non-Bridged)

The second key element in this invention involves the method by which the electrical circuit is completed. Electrical circuits described in prior art typically involve the use of bridge circuits, which are often complex and poorly suited for automation, in that the bridge circuits typically require an operator to manually balance the bridge.

Figure 3:
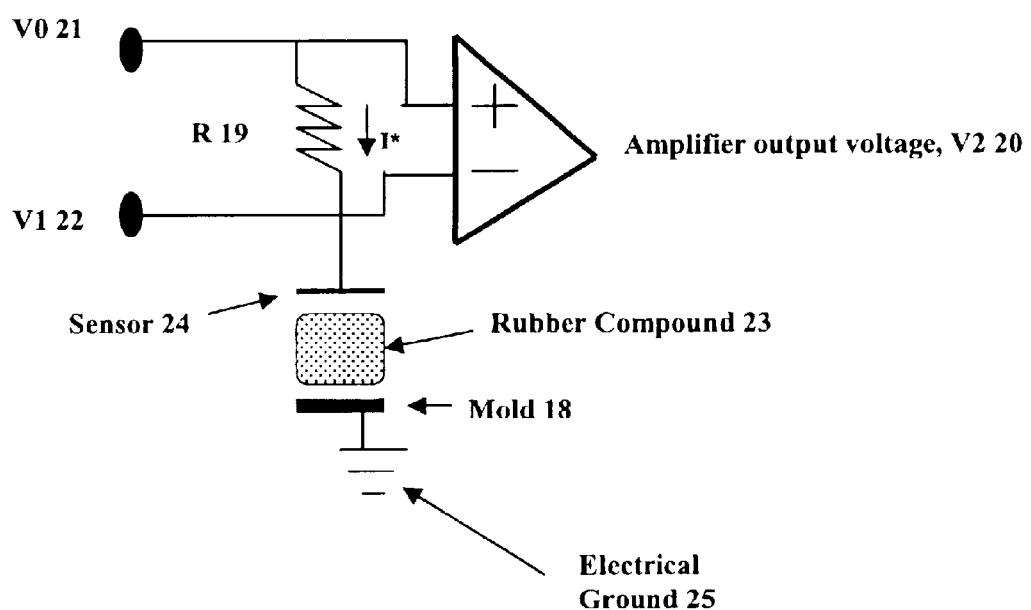
FIG. 3 Shows the sensor electrical circuit.

The sensor circuit used in this invention involves only a simple RC voltage divider, wherein the current is driven to the grounded 25 mold 18 (the opposing capacitor plate) through the curing rubber. A load resistor 19 (typically 200 k-ohm) is placed in line with the flow of current, and the resultant voltage 20, V2 across the resistor 19 is measured with a high precision amplifier. By simultaneously measuring the applied voltage (also known as the excitation voltage), it is then possible to readily determine the amount of attenuation and phase shift resultant from the flow of complex current. FIG. 3 illustrates the sensor electrical circuit, where the applied (excitation) voltage 21, V0=sin$\omega$t, is placed at one terminal of the amplifier, and this potential drives a complex current I* through the load resistor 19 (R) and then finally through the capacitor formed by the sensor 24, rubber compound 23, and the electrically grounded 25 mold 18.

The following description assumes a voltage amplitude of 1 volt for the excitation V0. However, all the subsequent analysis remains the same if the voltage is not unity; in the non-unity cases, k becomes the ratio of the negative pin voltage and the positive pin voltage.

From the illustration above, the excitation voltage 21 (V0=sin$\omega$t) drives a complex current (I*) through the resistor 19, R to ground 25. V0 is a digitally generated sine wave, generated by a high-speed data acquisition card, such as the PCI-MIO-16E4 card manufactured by National Instruments of Austin, Tex., that produces high quality sinusoidal signals at frequencies varying from 10 Hz to 10 kHz (as specified by the user). A voltage drop occurs across the load resistor 19, leaving an attenuated and phase shifted signal at the negative pin 22, V1=ksin($\omega$t+$\theta$)=k<$\theta$, where < is used to denote the term "at a phase angle of." The rubber compound 23 between the sensor 24 and electrically grounded 25 mold 18 provides a complex impedance of magnitude Z at phase angle $\Phi$. However, it is within the scope of the present invention that the upper range of the frequencies used by embodiments of the present invention may extend to 100kHz.

Element 3: Demodulation of the Sensor Signal.

Calculating Z and $\Phi$ is done by simultaneously digitally capturing the excitation signal V0 (sin($\omega$t)) and the amplifier output voltage V2 20, where V2=sin($\omega$t)−ksin($\omega$t+$\theta$). The previously referenced high-speed data acquisition card is used to digitize the signals V0 21 and V2 20, preserving the digital representation of the waveforms for further digital signal processing.

Provided with the digitally preserved signals V0 21 and V2 20, measurement of the quantities k and $\theta$ is done via standard demodulation practices, as is understood by one skilled in the art.

Once the quantities k and $\theta$ have been measured, determination of Z and $\Phi$ is done by analyzing the circuit described in FIG. 3.

i. I*=(V0−V1)/R ii. Z=V1/I* iii. Substituting, since V1=k<$\theta$ and V0=1 iv. Impedance (Z)=R*(k<$\theta$)/(1−k<$\theta$)=Z<$\Phi$ v. As can be seen in the equation above, the magnitude Z and phase angle are easily derived from the knowns, R, k, and $\theta$.

vi. Converting the polar number into a complex number separates out the real and imaginary components, resistance and reactance.

vii. Reactance (X)=Z sin$\Phi$=1/wC, where w=2$\pi$f viii. Resistance (R)=Zcos$\Phi$ ix. Converting these quantities into conductance and capacitance is accomplished by inverting the equations of vii and viii:

x. Capacitance (C)=1/(w*Zsin$\Phi$)

xi. Conductance (G)=1/Zcos$\Phi$

Figure 4:
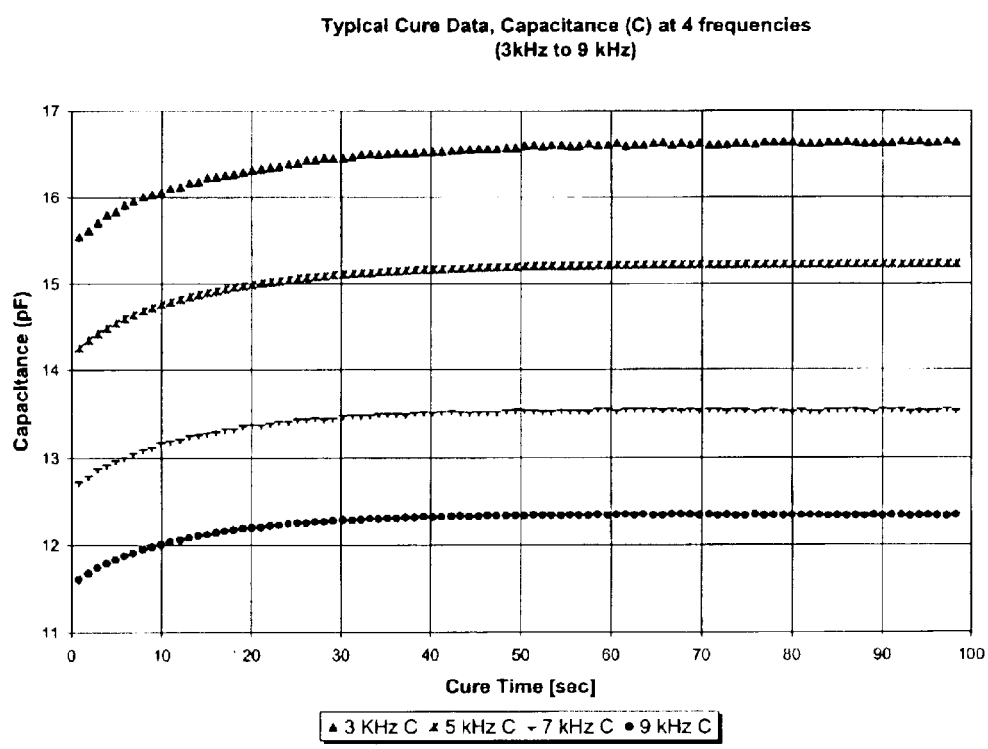
FIG. 4 Shows sensor capacitance data collected at 8 frequencies from 3 kHz to 10 kHz.
Figure 5:
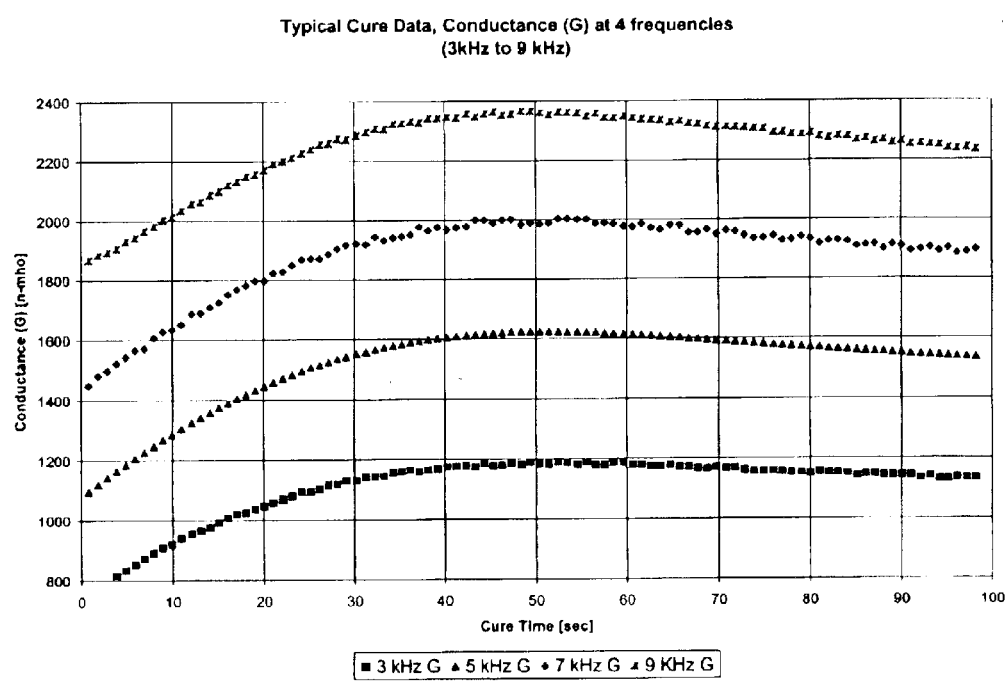
FIG. 5 Shows sensor conductance data collected at 8 frequencies from 3 kHz to 10 kHz.

Any of the data pairs (Z and $\Phi$, R and X, G and C) can then be used to represent the resultant cure data (also referred to as "process curves"). FIG. 4 shows a typical set of capacitance (C) data collected from a rubber cure, displaying data collected at 4 different excitation frequencies from 3 kHz to 9 kHz. FIG. 5 shows a typical set of conductance (G) data collected from the same rubber cure, displaying data collected at 4 different excitation frequencies from 3 kHz to 9 kHz.

Element 4: Methodology for Establishing Control Algorithms

Given that impedance property data (Z and $\Phi$, R and X, G and C) is observed and recorded during a cure, as depicted in FIGS. 4 and 5, the next step is to establish a control method that is capable of:

(1) measuring the impedance property data directly in the production process, and (2) reaching a conclusion with respect to proper cure time for a particular production cycle, based on the data measurement.

The process for algorithm development is outlined below:
Embodiment 1 (Algorithm Development using Production Mold and Rheometer):
(1) Identify the application of interest (type of part, type of compound, etc.)
(2) Install a sensor in the production mold, so that it can be used to obtain impedance property data on the curing rubber.
(3) As part of the algorithm development, define a range of cure conditions 26 or statistically designed experiment that encompass the range of variation expected to occur within normal production processes, and would also result in a range of proper or expected cure times.
  a. For example, a batch change would be expected to occur with normal production processes, and the new batch could also have a different curing characteristics, requiring a different cure time to reach optimal cure state. Similarly, a +/−5 degree F. change in mold temperature could also be expected, which would necessitate a different cure time to reach the same cure state.
  b. A typical defined range of cure conditions would involve a variety of a range of temperatures, as described below:

| Case number | Mold temperature | Batch number |
|---|---|---|
| 01 | 5 F. below nominal | Batch A |
| 02 | 5 F. below nominal | Batch B |
| 03 | 5 F. below nominal | Batch C |
| 04 | nominal | Batch A |
| 05 | nominal | Batch B |
| 06 | nominal | Batch C |
| 07 | 5 F. above nominal | Batch A |
| 08 | 5 F. above nominal | Batch B |
| 09 | 5 F. above nominal | Batch C |

(4) Now that a range of potential conditions has been defined, it is also possible to rheometrically determine an optimal cure time and/or a relative rate of cure for each of the conditions. A typical optimal cure time target might be the T90 time, the time that the curing rubber reaches 90% of its final elastic torque maximum, although other cure state times are also appropriate targets (T50, T75, etc.). So for each of the cure conditions described in the table above, it is possible to set the rheometer to the specified temperature, enter the specified batch, and measure the proper T90 time 27. An example of the type would appear as follows:

| Case number | Mold temperature | Batch number | Proper Cure time (T90: seconds) |
|---|---|---|---|
| 01 | 5 F. below nominal | Batch A | 120 |
| 02 | 5 F. below nominal | Batch B | 135 |
| 03 | 5 F. below nominal | Batch C | 142 |
| 04 | nominal | Batch A | 100 |
| 05 | nominal | Batch B | 110 |
| 06 | nominal | Batch C | 115 |
| 07 | 5 F. above nominal | Batch A | 90 |
| 08 | 5 F. above nominal | Batch B | 95 |
| 09 | 5 F. above nominal | Batch C | 98 |

Fundamentally, the purpose of the rheometry is to establish the relative cure rates under various conditions. Since in-mold conditions will vary significantly from rheometric instrument conditions, the optimum production cure time may not be the same as the T90 time from the rheometer. However, the rheometer data does provide useful information regarding the relative cure rates and times observed due to rubber compound batch and cure variations.

(5) Now that information exists regarding the effects of process variation on proper cure time as measured by rheometric means, it is necessary to simulate those conditions in the production mold, and to observe the resultant impedance property data during those cures 28. Multiple replicates of the cure conditions are ideal—at least three replicates are recommended. Therefore, in this example, the production mold is set at a temperature 5 degrees below nominal, and batch A is used as the compound. Three cures are conducted while recording the impedance data, which appears in the form FIGS. 4 and 5. Then the compound is changed to batch B and and three cures are recorded, etc. When complete, the impedance data files will be associated with each cure condition as described in the table below:

| Case number | Mold temperature | Batch number | Proper Cure time (T90:seconds) | Associated impedance files |
|---|---|---|---|---|
| 01 | 5 F. below nominal | Batch A | 120 | 01, 02, 03 |
| 02 | 5 F. below nominal | Batch B | 135 | 04, 05, 06 |
| 03 | 5 F. below nominal | Batch C | 142 | 07, 08, 09 |
| 04 | nominal | Batch A | 100 | 10, 11, 12 |
| 05 | nominal | Batch B | 110 | 13, 14, 15 |
| 06 | nominal | Batch C | 115 | 16, 17, 18 |
| 07 | 5 F. above nominal | Batch A | 90 | 19, 20, 21 |
| 08 | 5 F. above nominal | Batch B | 95 | 22, 23, 24 |
| 09 | 5 F. above nominal | Batch C | 98 | 25, 26, 27 |

(6) Given that these conditions have been set in both the rheometer and in the mold, the next step involves searching for a statistical correlation between the rheometrically-determined T90 times and the impedance data. In other words, the impedance data must be searched for measures that reflect the cure state. In order to mathematically determine the correlation, it is necessary to measure the impedance data in some fashion. Measurements are performed as follows:
  a. Each data stream (a data stream is a Z, $\Phi$, R, X, G or C plot versus time at a specific frequency) is divided into 5 or more specific time segments or "windows".
    i. Using software written in LabView, available from National Instruments, Austin, Tex., the segment start time, stop time, and length can be automatically generated using preset values or custom-specified by the user using the software.
    ii. The first three segments are fixed segments, with specified start time, stop time, and length. The fourth and fifth segments are known as variable segments, in which the fixed length measurement is measured only after the data stream travels through a maximum or minimum value of an impedance property (Z, $\Phi$, R, X, G or C).
  b. Each segment is then measured in the following eight ways:
    i. The maximum value is recorded.
    ii. The time of the maximum value is recorded.
    iii. The minimum value is recorded.

iv. The time of the minimum value is recorded.

v. The integrated area under the segment is recorded.

vi. A linear least-squares best fit is done to the segment data, and the slope of the line is recorded. [m, in the equation y=mx+b].

vii. An exponential best fit is done to the segment data, and the damping coefficient is recorded. [$\alpha$, in the equation y=Ae$^{-\alpha x}$].

viii. An exponential best fit is done to the segment data, and the amplitude coefficient is recorded. [A, in the equation y=Ae$^{-\alpha x}$].

(7) Following the completion of measurements a data table is created 29 as follows (only a portion of the table is shown—a total of 640 impedance measurements are typically made on each file: 8 frequencies times 2 data types (R and X, G and C, or Z and $\Phi$) times 5 window times 8 measurement types=640 measurements)

| File number | Mold temperature | Batch number | Proper Cure time (T90: seconds) | Window 1, data stream 1, slope | Window 1, data stream 1, max | Window 1, data stream 1, time of max |
|---|---|---|---|---|---|---|
| 01 | 5 F. below nominal | Batch A | 120 | .117 | 10.13 | 48 |
| 02 | 5 F. below nominal | Batch A | 120 | .114 | 10.21 | 48 |
| 03 | 5 F. below nominal | Batch A | 120 | .112 | 10.24 | 49 |
| 04 | 5 F. below nominal | Batch B | 135 | .105 | 10.25 | 51 |
| 05 | 5 F. below nominal | Batch B | 135 | .105 | 10.13 | 51 |
| 06 | 5 F. below nominal | Batch B | 135 | .108 | 10.18 | 51 |
| 07 | 5 F. below nominal | Batch C | 142 | .099 | 10.33 | 53 |
| 08 | 5 F. above nominal | Batch C | 142 | .098 | 10.09 | 52 |
| 09 | 5 F. above nominal | Batch C | 142 | .101 | 10.20 | 53 |
| 10 | nominal | Batch A | 100 | .156 | 10.33 | 39 |
| Etc. | | | | | | |

Figure 6:
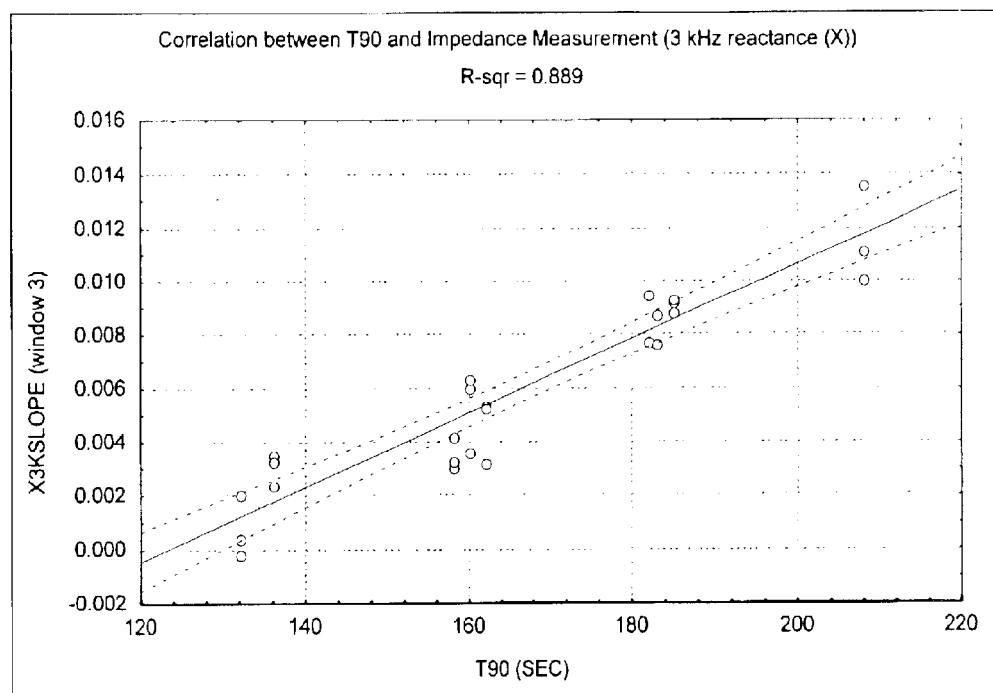
FIG. 6 Shows the correlation between observed T90 times and an impedance measurement.

Given that there are now a large number of measurements, it is then possible to search through all the measurements to find a measure that appears to most strongly reflect the rate of cure. This is done by finding the measures with the highest correlation to the rheometry data 30. Software, written in LabView, available from National Instruments, Austin, Tex., systematically performs a correlation between the T90 data and the measurements, and then ranks and returns the measurements that are most reflective of cure rate. FIG. 6 shows a typical correlation between observed T90 times and an impedance measurement.

Not only does the correlation help identify the measures that are most reflective of cure rate, it also defines how the measure is used. The plot of the best-fit line in FIG. 6 can be written in the form: T90=A*(X3Kslope)+B.

Therefore, for the machine to decide on a proper cure time for each cure, all it has to do is to measure the term (X3Kslope) in the defined measurement window, and then the measured value is inserted into the equation above with the coefficients A and B. The resultant time output is the proper cure time for that cure cycle.

The correlation value can also be improved through the use of multiple regression 31. Since there are a variety of additional measurements available, a combination of these measurements can provide a better reflection of cure state. The previously mentioned software culls out the top 20 measurements (highest correlation to T90) and then reviews all possible 4 term multiple regressions, returning the multiple regression equation with the best R-squared correlation in the form of:

$$T90 = A1*Z1 + A2*Z2 + A3*Z3 + A4*Z4 + B$$

where all the A terms and B terms are coefficients, and all the Z terms are some form of impedance property measurement as previously defined. Therefore, the control system need only to make the 4 measurements and insert them into the equation in order to calculate the proper cure time.

Figure 7:
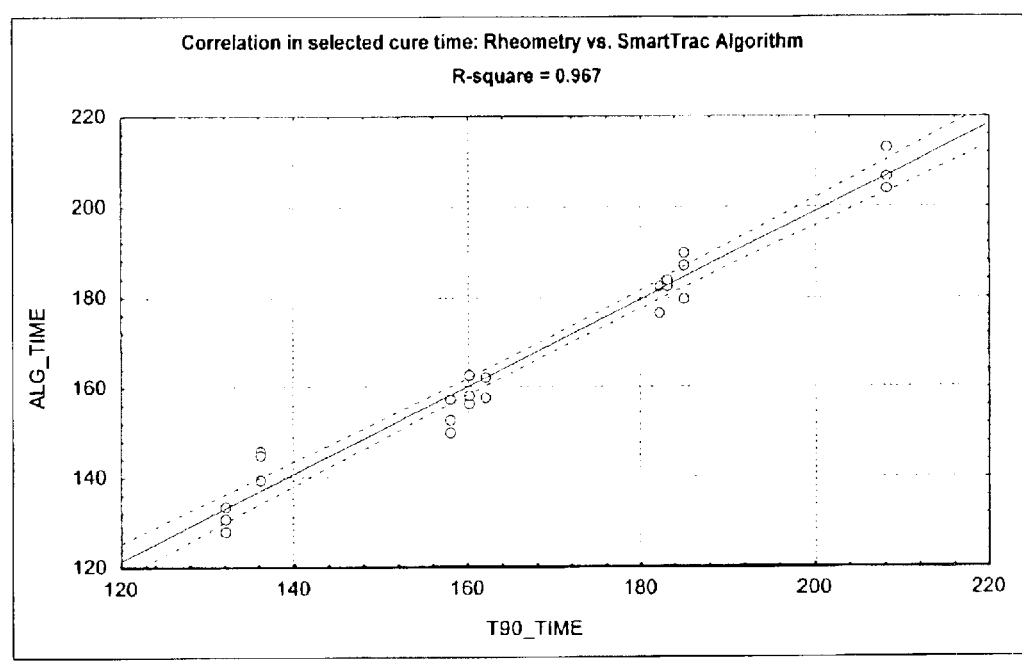
FIG. 7 Shows the correlation between observed T90 times and 4-term multiple regression of impedance measurements.

FIG. 7 shows a plot of the resultant algorithm selected cure times versus the T90 times, using a four-term multiple regression. Note the improvement in R-square from 0.889 to 0.967.

Figure 8:
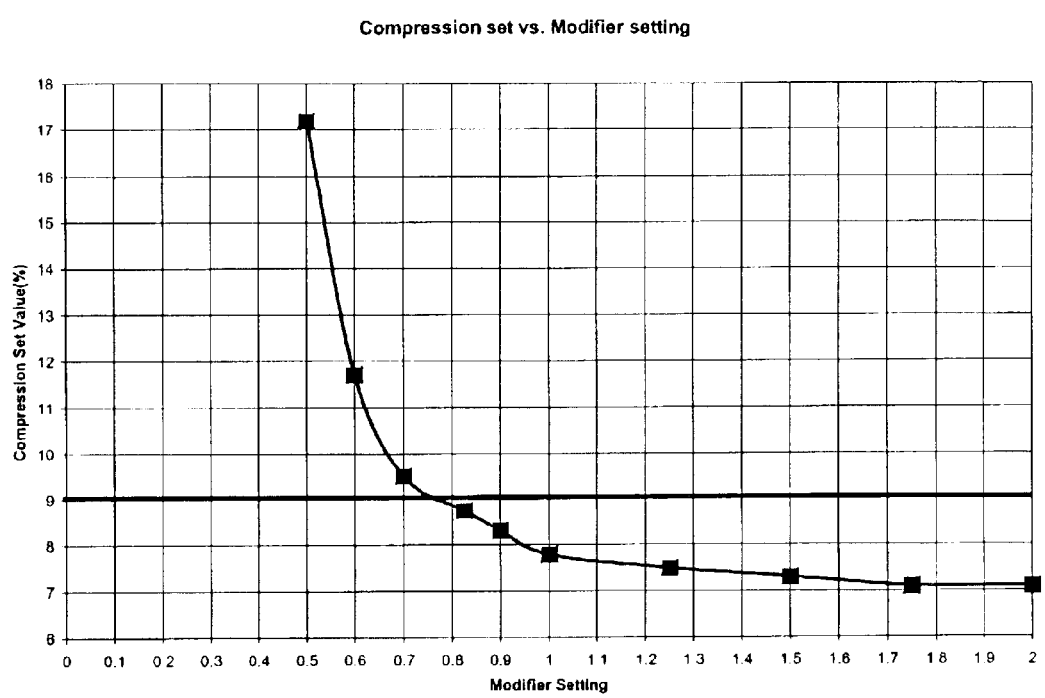
FIG. 8 Shows a plot of modifier setting versus a specific part property (compression set).

(8) At this point the cure control equation is defined, with the exception that the equation is truly only responsive to changes in the process that effect cure rate, and it does not necessarily provide the specific cure state desired. This is due to the fact that the rheometric T90 times used in the correlation are only relative and may not provide the specific property desired in the production-molded product. In order to adjust the cure control equation to provide the true optimum cure time, it also has a linear adjustment (known as "the modifier") that will allow it to operate at some multiple of its standard output. The modifier is factored into the cure control equation as follows:

$$T90[optimized] = (modifier)*(A1*Z1 + A2*Z2 + A3*Z3 + A4*Z4 + B)$$

a. In order to determine the optimum modifier setting, the production press is run with the control system controlling the cure time 32. The modifier setting is changed over a relatively large range, in several increments, and the resultant part properties are measured. In this way, a plot of part property (i.e. spring constant, compression set, dynamic stiffness, etc) versus. modifier setting can be developed. Multiple parts should be produced to get a good representative property. An example plot is shown in FIG. 8.

In the example previously discussed, a customer may desire to consistently have compression set values of less than a certain amount (9%, for example). Given that specification, it is clear that a modifier of at least 0.8 would be required, and to include some safety factor, 0.9 may be more appropriate. Any higher modifier setting will simply extend cure time without improving compression set. Any lower modifier setting will not provide the specified compression set value. After choosing the appropriate modifier the algorithm is ready to be used to control the process 33.

Figure 9:
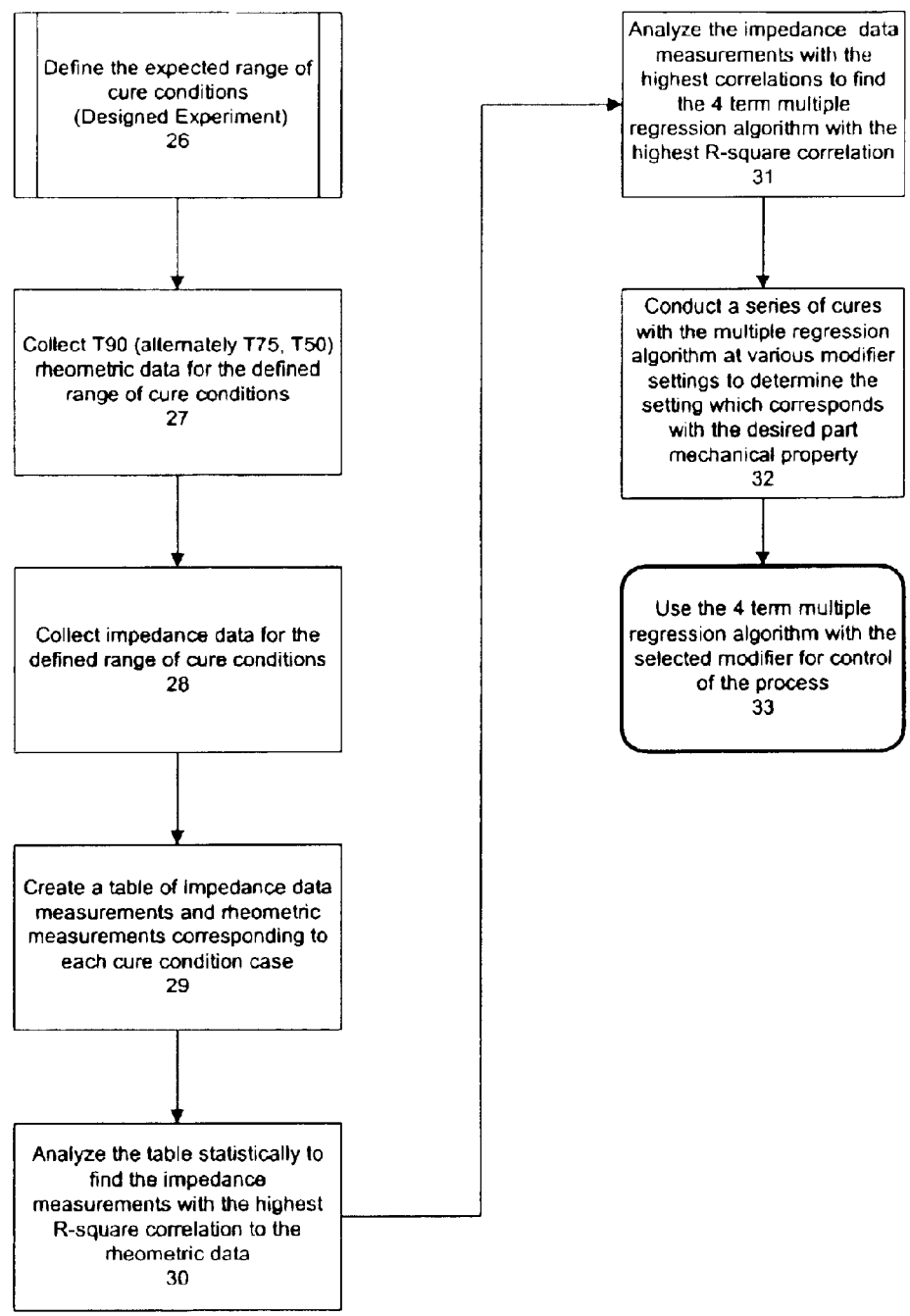
FIG. 9 Shows the Control Algorithm development logic.

The process for developing a control algorithm described in Embodiment 1 is also shown in FIG. 9.

Embodiment 2 (Algorithm Development using Rheometer Only):

In an alternate embodiment of the invention, a production press need not be used for the initial stages of the algorithm development. Instead, a sensor can be installed directly into the rheometer, and the impedance data and rheometry can be collected simultaneously. A production press is still required to set the modifier, as described in Step 8 of Element 4.

Element 5: Real-Time Control Application

Figure 10:
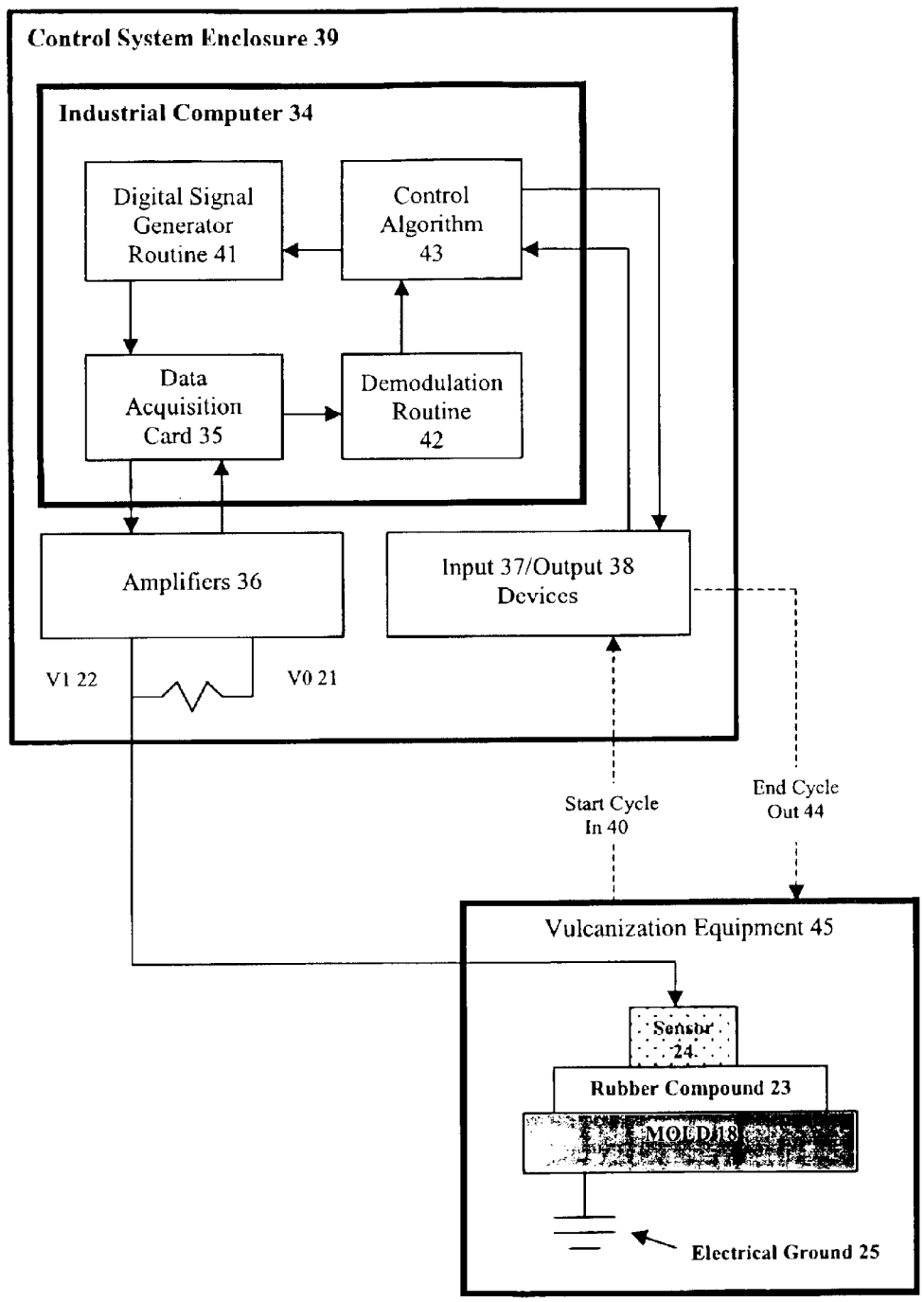
FIG. 10 Shows the Control System schematic.

The control system and its relationship to the vulcanization equipment 45 is shown in FIG. 10. The control unit is equipped with:

(1) An industrial computer 34, for processing data as described above.
(2) A control algorithm 43.
(3) A data acquisition card 35, installed in the computer, for
   i. Generating sinusoidal excitation voltages.
   ii. Reading and digitizing amplifier outputs.
(4) A digital signal generator software routine 41.
(5) A digital signal demodulation software routine 42.
(6) Amplifiers 36 for collection of real-time impedance data.
(7) Digital inputs 37 for receiving indications of when a cycle has started, or rubber compound injected, or other key discrete data.
(8) Digital outputs 38 for notifying operators of end-of-cure, or energizing relays that open the press, or providing other key discrete outputs.
(9) An enclosure 39 to protect and isolate the components.

Figure 11:
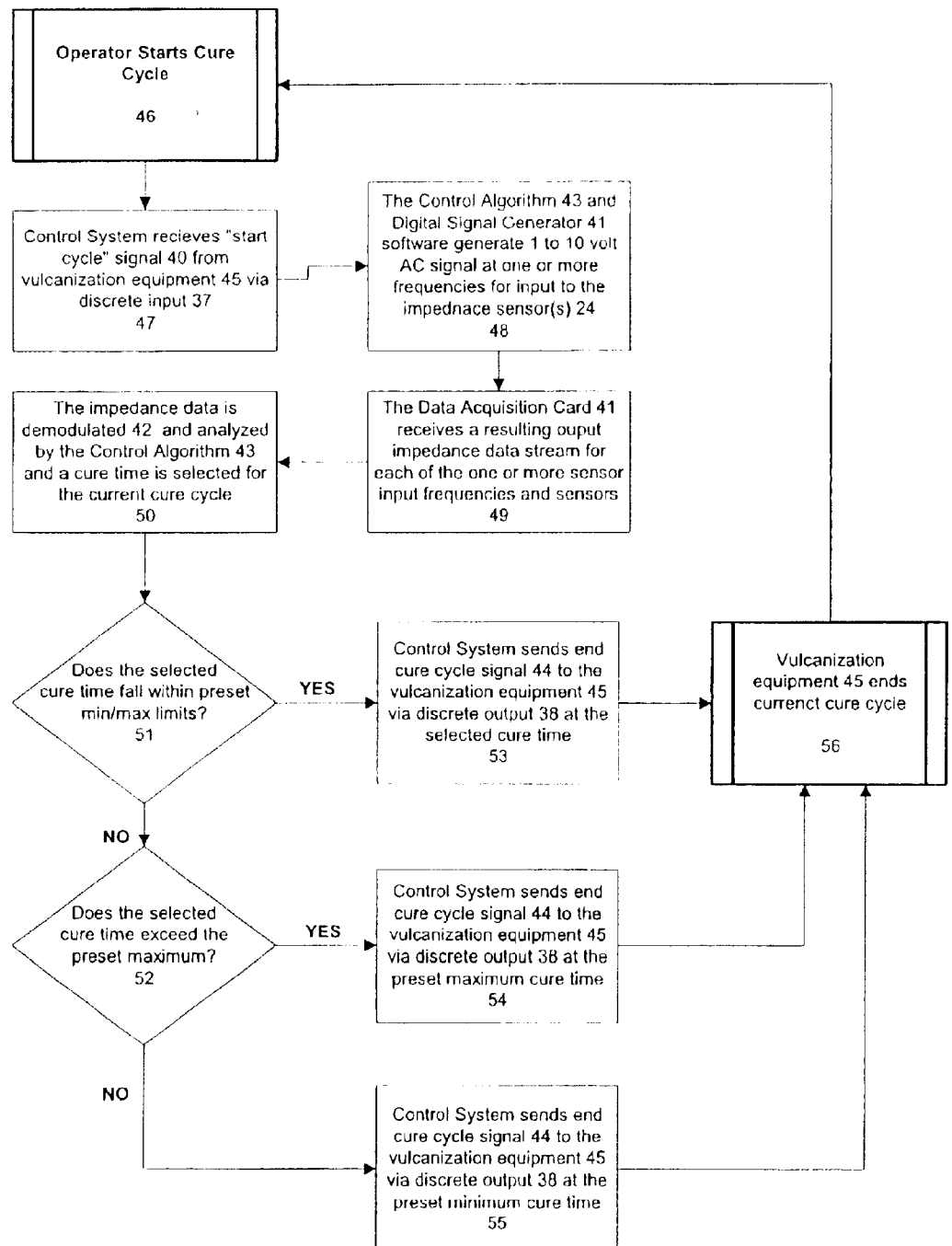
FIG. 11 Shows the Control System logic.

The actual control of the production press is a relatively straight-forward process as shown in FIG. 11. The process can be summarized as follows:

(1) When the equipment operator starts a new production cycle 46, a digital input 37 is energized 40 from the vulcanization equipment 45 that tells the control algorithm 43 that the cycle has started 47.
(2) The digital signal generator routine 41 and data acquisition card 35 then generates digital sinusoidal excitations for one or more sensors 48, as defined by the control algorithm 43 (for example, 1 kHz, 5 kHz, 7 kHz and 9 kHz could be the required frequencies as specified by the algorithm created in Element 4).
(3) The data acquisition card 35 and demodulation routine 42 then reads the sensor(s) response 49.
(4) The demodulated sensor response is recorded by the computer 34 in pairs of impedance data (Z and Φ, R and X, or G and C) 50.
(5) The data is then segmented and measured as required by the control algorithm 43 defined in Element 4 50.
(6) The measurements are then entered into the control algorithm 43 equation:

$$T90[optimized]=(modifier)*(A1*Z1+A2*Z2+A3*Z3+A4*Z4+B)$$

The calculated cure time to achieve the desired part mechanical property is the product of the equation 50.

(7) When the calculated cure time has elapsed, a digital output 38 is energized 44 to open the vulcanization equipment 45,51,53,56.
(8) If required by the process, the control algorithm 43 is capable of comparing the calculated cure time to user-defined minimum and maximum cure times and using those times as alternative criteria to end the process 52,54,55,56.

While various embodiments of the present invention have been described in detail, it is apparent that modifications and adaptations of those embodiments will occur to those skilled in the art. It is to be expressly understood, however, that modifications and adaptations are within the scope of the present invention, as set forth in the following claims.

What is claimed is:

1. A process for curing a rubber part composed of natural or synthetic rubber with fillers using vulcanization equipment, comprising:
   a) measuring curing conditions by dielectric or impedance means applied on opposite sides and through the rubber part or a witness cavity representing the part during the curing process to produce a process curve for a specific rubber compound, wherein said process curve is correlated with a one or more rheometric properties of the rubber compound and one or more desired or specified mechanical properties of the rubber part;
   b) analyzing the process curve for the specific rubber compound with a software algorithm which defines and quantifies a correlation relationship between the process curve and the rheometric properties of the rubber compound and the desired or specified part mechanical properties; and
   c) applying the correlation relationship in real-time to end the curing process and thereby produce rubber part(s) of uniform quality and with reduced process cycle time.

2. The process of claim 1, in which the dielectric or impedance measurement circuit is non-bridged.

3. The process of claim 1, in which the correlation is accomplished using a defined range of cure conditions or a statistically designed experiment.

4. The process of claim 1, in which the correlation is accomplished using an impedance sensor installed in ODR, MDR, or similar rheometric instrument.

5. The process of claim 1, in which the said software algorithm identifies and uses a Maximum Value, and/or Time of Maximum Value in a specific time segment of the process curve to calculate the end of cure time.

6. The process of claim 1, in which the said software algorithm identifies and uses a Minimum Value, and/or Time of Minimum Value in a specific time segment of the process curve to calculate the end of cure time.

7. The process of claim 1, wherein said algorithm uses a rate of a cure determined using a linear least-squares best fit over a specified time segment of the process curve for obtaining a slope (m) of a line equation: $y=mx+b$ that is a linear approximation of the process curve in the specified time segment, wherein the variable x in the line equation represents a time in the specified time segment, the variable y in the line equation represents an impedance value that approximates the process curve at the time for the variable x, and the constant b in the line equation represents an impedance value that approximates the process curve when x is zero.

8. The process of claim 1, wherein said algorithm uses a rate of a cure determined using an exponential best fit over a specified time segment of the process curve for obtaining a damping coefficient, α, from an equation: $y=Ae^{\alpha x}$, that is an approximation of the process curve in the specified time segment, wherein the variable x in the equation represents a time in the specified time segment, the variable y in the equation represents an impedance value that approximates the process curve at the time for the variable x, and the constant A in the equation represents an amplitude coefficient.

9. The process of claim 1, wherein said algorithm uses a rate of a cure determined using an exponential best fit over a specified time segment of the process curve for obtaining an amplitude coefficient, A, from an equation: $y=Ae^{\alpha x}$, that is an approximation of the process curve in the specified time segment, wherein the variable x in the equation represents a time in the specified time segment, the variable y in the equation represents an impedance value that approximates the process curve at the time for the variable x, and the constant a in the equation represents a damping coefficient.

10. The process of claim 1, in which the said algorithm uses the integrated area under the process curve or a portion of the curve to calculate the end of cure time.

11. The process of claim 1, in which the dielectric or impedance measurements include impedance (Z), phase angle (Φ), resistance (R), reactance (X), conductance (G) or capacitance (C) values as the dependent variable of the process curve as plotted against time as the dependent variable.

12. The process of claim 1, in which the correlation is made between mathematical measurements of the process curve and rheometric property measurements of the rubber compound and to the desired or specified part mechanical properties such as tensile strength, compression set, dynamic stiffness, or elastic torque.

13. The process of claim 12, in which a final correlation to the part mechanical properties is made with a modifier which provides a linear adjustment to a T90 or rheometric correlation equation.

14. The process of claim 1, in which the impedance measurements are made at a frequency of about 10 Hz to 100 kHz.

15. The process of claim 1, in which said natural and synthetic rubber compounds are selected from the group consisting of: styrene-butadiene, polybutadiene, polyisoprene, ethylene-propylene, butyl, halobutyl, nitrile, polyacrylic, neoprene, hypalon, silicone, fluorcarbon elastomers, polyurethane elastomers, and mixtures thereof.

16. The process of claim 15, in which rubber compound fillers include carbon black, clays, oils, silicas, and the like.

17. The process of claim 1, in which the said process is controlled using a computer.

18. The process of claim 17, in which said computer controls the process by receiving a "start cure" signal from the vulcanization equipment and based on a predefined software algorithm sends an "end cure" signal back to the vulcanization equipment.

19. The process of claim 1, in which the rubber part is processed using the vulcanization equipment and its associated tooling and an impedance measuring means for measuring impedance related signals indicative of a curing state of the rubber part, wherein said impedance measuring means includes one or more of the vulcanization equipment and its associated tooling.

20. The process of claim 19, in which the impedance measuring means includes a primary sensor electrode coupled with an opposing grounded surface electrode, which is part of the vulcanization equipment or its associated tooling.

21. The process of claim 19, in which the impedance measuring means includes an impedance sensor is in contact with the part or in contact with the witness cavity that is filled with the rubber compound and is representative of the part.

22. The process of claim 21, in which the impedance sensor includes an additional guard electrode to help preclude the primary electrode from fringing or becoming non-linear.

23. The process of claim 22, in which the impedance sensor primary and guard electrodes are separated from the rubber compound being processed by alumina ceramic or other stable and abrasion resistant dielectric material.

24. The process of claim 20, in which the impedance sensor primary electrode, a guard electrode, and a housing are separated electrically from each other by a dielectrically stable polymer such as cyanate ester and alumina ceramic.

25. The process of claim 20, in which the impedance sensor primary electrode, a guard electrode, and a housing are fused together and separated electrically from each other by glass or glass doped with alumina ceramic or other like material.

26. The process of claim 20, in which the primary sensor electrode and a guard electrode are embedded in a metallized and layered ceramic circuit.

27. The process of claim 20, in which the primary sensor electrode, a guard electrode, and a housing are press fit together and separated electrically from each other and the rubber compound being cured by a diamond or diamond like coating.

28. The process of claim 18, in which said vulcanization equipment includes one of: injection molding machines, compression and transfer molding presses, belt making presses, autoclaves and tire molding machines.

29. The process of claim 19, in which said associated tooling includes: injection molds, compression and transfer molds, mandrels, platens, tire molds.

30. The process of claim 18, wherein said dielectric or impedance means includes more than one sensor to monitor the process, and one of the sensors that lags from cycle-to-cycle is used to control the end point of a cure cycle.

* * * * *